US00PP18269P2

(12) United States Plant Patent
Takeshita

(10) Patent No.: US PP18,269 P2
(45) Date of Patent: Dec. 4, 2007

(54) ***NEMESIA* PLANT NAMED 'KIRINE-12'**

(50) Latin Name: ***Nemesia caerulea*×*Nemesia strumosa***
Varietal Denomination: Kirine-12

(75) Inventor: Daigaku Takeshita, Tochigi-ken (JP)

(73) Assignee: Kirin Brewery Co. Ltd., Tokyo (JP)

( * ) Notice: Subject to any disclaimer, the term of this patent is extended or adjusted under 35 U.S.C. 154(b) by 0 days.

(21) Appl. No.: 11/489,223

(22) Filed: Jul. 19, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Nemesia* plant named 'Kirine-12', characterized by its upright, outwardly spreading and mounded growth habit; freely branching and flowering plant habit; large apricot pink-colored flowers; relatively to high temperatures; and good garden performance.

1 Drawing Sheet

Cross-Reference to Related Applications: *Nemesia* Plant Named 'Kirine-9'; applicant, Daigaku Takeshita; U.S. Plant patent application Ser. No. 11/489,224. *Nemesia* Plant Named 'Kirine-13'; applicant, Daigaku Takeshita; U.S. Plant patent application Ser. No. 11/489,169. *Nemesia* Plant Named 'Kirine-14'; applicant, Daigaku Takeshita; U.S. Plant patent application Ser. No. 11/489,164. *Nemesia* Plant Named 'Kirine-15'; applicant, Daigaku Takeshita; U.S. Plant patent application Ser. No. 11/489,404.

Botanical designation: *Nemesia caerulea*×*Nemesia strumosa.*

Cultivar denomination: 'KIRINE-12'.

BACKGROUND OF THE INVENTION

The present invention relates to a new and distinct cultivar of *Nemesia,* botanically known as *Nemesia caerulea*× *Nemesia strumosa* and hereinafter referred to by the name 'Kirine-12'.

The new *Nemesia* is a product of a planned breeding program conducted by the Inventor in Tochigi, Japan. The objective of the breeding program is to create new *Nemesia* cultivars with good vigor and attractive flower coloration.

The new *Nemesia* originated from a cross-pollination made by the Inventor in March, 2004 in Tochigi, Japan of the *Nemesia caerulea* cultivar White Wings, not patented, as the female, or seed, parent with the *Nemesia strumosa* cultivar Nebula Orange, not patented, as the male, or pollen, parent. The new *Nemesia* was discovered and selected by the Inventor as a single flowering plant within the progeny of the stated cross-pollination in a controlled environment in Tochigi, Japan in September, 2004.

Asexual reproduction of the new *Nemesia* by terminal cuttings in a controlled environment in Tochigi, Japan since October, 2004, has shown that the unique features of this new *Nemesia* are stable and reproduced true to type in successive generations.

SUMMARY OF THE INVENTION

The cultivar Kirine-12 has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Kirine-12'. These characteristics in combination distinguish 'Kirine-12' as a new and distinct cultivar of *Nemesia:*

1. Upright, outwardly spread and mounded growth habit.
2. Freely branching and flowering plant habit.
3. Large apricot pink-colored flowers.
4. Relatively tolerant to high temperatures.
5. Good garden performance.

Plants of the new *Nemesia* differ from plants of the female parent, the cultivar White Wings, in the following characteristics:

1. Plants of the new *Nemesia* are larger than plants of the cultivar White Wings.
2. Plants of the new *Nemesia* have larger flowers than plants of the cultivar White Wings.
3. Plants of the new *Nemesia* and the cultivar White Wings differ in flower color as plants of the cultivar White Wings have white-colored flowers.

Plants of the new *Nemesia* differ from plants of the male parent, the cultivar Nebula Orange, in the following characteristics:

1. Plants of the new *Nemesia* are larger than plants of the cultivar Nebula Orange.
2. Flowers of plants of the new *Nemesia* are fragrant whereas flowers of plants of the cultivar Nebula Orange are not fragrant.
3. Plants of the new *Nemesia* and the cultivar Nebula Orange differ in flower color as plants of the cultivar Nebula Orange have orange-colored flowers.
4. Plants of the new *Nemesia* are more tolerant to high temperatures than plants of the cultivar Nebula Orange.

Plants of the new *Nemesia* differ from plants of the cultivars Kirine-9, disclosed in a U.S. Plant patent application Ser. No. 11/489,224; Kirine-13, disclosed in a U.S. Plant patent application Ser. No. 11/489,169; Kirine-14, disclosed in a U.S. Plant patent application Ser. No. 11/489,164; and Kirine-15, disclosed in a U.S. Plant patent application Ser. No. 11/489,404, primarily in flower color.

Plants of the new *Nemesia* can be compared to plants of the cultivar Inupcream, disclosed in U.S. Plant patent application Ser. No. 11/174,962. In side-by-side comparisons conducted by the Inventor in Tochigi, Japan, plants of the new *Nemesia* differed from plants of the cultivar Inupcream in the following characteristics:

1. Plants of the new *Nemesia* were more mounded than plants of the cultivar Inupcream.
2. Plants of the new *Nemesia* had larger leaves and flowers than plants of the cultivar Inupcream.
3. Plants of the new *Nemesia* and the cultivar Inupcream differed in flower color.
4. Plants of the new *Nemesia* were more high temperature tolerant than plants of the cultivar Inupcream.

BRIEF DESCRIPTION OF THE PHOTOGRAPH

The accompanying colored photograph illustrates the overall appearance of the new *Nemesia,* showing the colors as true as it is reasonably possible to obtain in colored reproductions of this type. Colors in the photograph may differ slightly from the color values cited in the detailed botanical description which accurately describe the colors of the new *Nemesia.* The photograph comprises a side perspective view of a typical flowering plant of 'Kirine-12' grown in a container.

DETAILED BOTANICAL DESCRIPTION

In the following description, color references are made to The Royal Horticultural Society Colour Chart, 1995 Edition, except where general terms of ordinary dictionary significance are used. Plants used for the aforementioned photograph and following description were grown under conditions which closely approximate commercial production conditions during the late spring in a polyethylene-covered greenhouse in Santa Paula, Calif. for about 10 to 13 weeks in 15-cm containers. During the production of the plants, day temperatures ranged from 16° to 27° C., night temperatures ranged from 7° to 15° C. and light levels ranged from 5,000 to 7,000 foot-candles. Plants were pinched one time about four weeks after planting.

Botanical classification: *Nemesia caerulea* cultivar Kirine-2.

Parentage:

*Female, or seed, parent.*—*Nemesia caerulea* cultivar White Wings, not patented.

*Male, or pollen, parent.*—*Nemesia strumosa* cultivar Nebula Orange, not patented.

Propagation:

*Type.*—By terminal cuttings.

*Time to initiate roots, summer.*—About 3 days at 23° C.

*Time to initiate roots, winter.*—About 5 days at 20° C.

*Time to produce a rooted young plant, summer.*—About 21 days at 23° C.

*Time to produce a rooted young plant, winter.*—About 23 days at 20° C.

*Root description.*—Fine, fibrous; white in color.

*Rooting habit.*—Freely branching; moderately dense.

Plant description:

*Plant and growth habit.*—Upright, outwardly spreading and mounded growth habit. Freely branching; about seven primary branches per plant and numerous secondary branches. Moderately vigorous growth habit.

*Plant height.*—About 24 cm.

*Plant diameter.*—About 34 cm.

Lateral branch description:

*Length.*—About 24 cm.

*Diameter.*—About 2.5 mm.

*Internode length.*—About 2.2 cm.

*Strength.*—Strong.

*Aspect.*—Initially upright to somewhat outwardly spreading.

*Texture.*—Smooth, glabrous.

*Color.*—144A.

Foliage description:

*Arrangement.*—Opposite, simple; sessile.

*Length.*—About 3.8 cm.

*Width.*—About 9 mm.

*Shape.*—Lanceolate.

*Apex.*—Acute.

*Base.*—Truncate.

*Margin.*—Slightly serrate.

*Texture, upper and lower surfaces.*—Smooth, glabrous.

*Venation pattern.*—Pinnate; arcuate.

*Color.*—Developing foliage, upper surface: 137A. Developing foliage, lower surface: 137B. Fully expanded foliage, upper surface: 137B; venation, 137C. Fully expanded foliage, lower surface: 137C; venation, 137C.

Flower description:

*Flower arrangement and habit.*—Zygomorphic solitary flowers arranged on terminal racemes; flowering acropetally towards the apex. Flowers bilabiate. Flowers face upright and outwardly. Flowers last about one week on the plant. Flowers not persistent. Freely flowering habit with about 40 to 45 flowers per raceme.

*Fragrance.*—Faint; floral.

*Natural flowering season.*—In California, plants flower from early spring to fall; flowering continuous during this period.

*Inflorescence height.*—About 7 cm.

*Inflorescence diameter.*—About 5 cm.

*Flower length.*—About 1.9 cm.

*Flower width.*—About 1.8 cm.

*Flower depth.*—About 1.5 cm.

*Flower buds.*—Shape: Ovoid. Length: About 1 cm. Diameter: About 6 mm. Color: 69A.

*Petals.*—Arrangement: Five petals; four upper petals are fused at base to form an upright lobed and arched banner lip; lower petal modified into a large lip with convex oval protuberance with serves as a pollinator nectar guided and landing platform. Shape: Rounded to oval. Apex: Rounded. Margin: Entire; lower lip, sinnuate. Length: Upper petals: About 7 mm. Lower petal: About 1.2 cm. Width: Upper petals: About 5 mm. Lower petal: About 1.8 cm. Texture, upper and lower surfaces: Smooth, glabrous; velvety. Color: When opening, upper surface: 182A. When opening, lower surface: 75B. Fully opened, upper surface: Upper petals, 181C, becoming closer to more grey than 186C with development; lower petal, 35A to 35B, becoming closer to more grey than 186C with development; protuberance, 33A, becoming closer to 162A with development; nectar guides, 79B. Fully opened, lower surfaces: Slightly more grey than 71C.

*Sepals.*—Arrangement: Calyx star-shaped with five sepals fused at the base. Shape: Narrowly elliptic.

Apex: Acute. Margin: Entire. Length: About 3 mm. Width: About 1 mm. Texture, upper and lower surfaces: Pubescent. Color, upper and lower surfaces: 137A.

*Peduncles.*—Length: About 3.2 cm. Diameter: About 2 mm. Angle: Erect to about 45° From vertical. Strength: Strong. Texture: Smooth, glabrous. Color: 137B.

*Pedicels.*—Length: About 1.8 cm. Diameter: About 1 mm. Angle: About 30° to 45° from peduncle axis. Strength: Strong. Texture: Pubescent; minute. Color: 146B.

*Reproductive organs.*—Stamens: Quantity/arrangement: Four per flower. Anther shape: Oval. Anther length: Less than 1 mm. Anther color: 162A. Pollen amount: Scarce. Pollen color: 162C. Pistils: Quantity: One per flower. Pistil length: About 3 mm. Style length: About 1 mm. Style color: 145D. Stigma shape: Rounded. Stigma color: 145D. Ovary color: 145A. Seed/fruit: Seed and fruit development have not been observed on plants of the new *Nemesia.*

Pathogen/pest resistance: Plants of the new *Nemesia* have not been observed to be resistant to pests and pathogens common to *Nemesia.*

Garden performance: Plants of the new *Nemesia* have been observed to tolerate wind and rain and have good garden performance.

Temperature tolerance: Plants of the new *Nemesia* have been observed to tolerate temperatures from about 4° C. to about 28° C.

It is claimed:

1. A new and distinct *Nemesia* plant named 'Kirine-12' as illustrated and described.

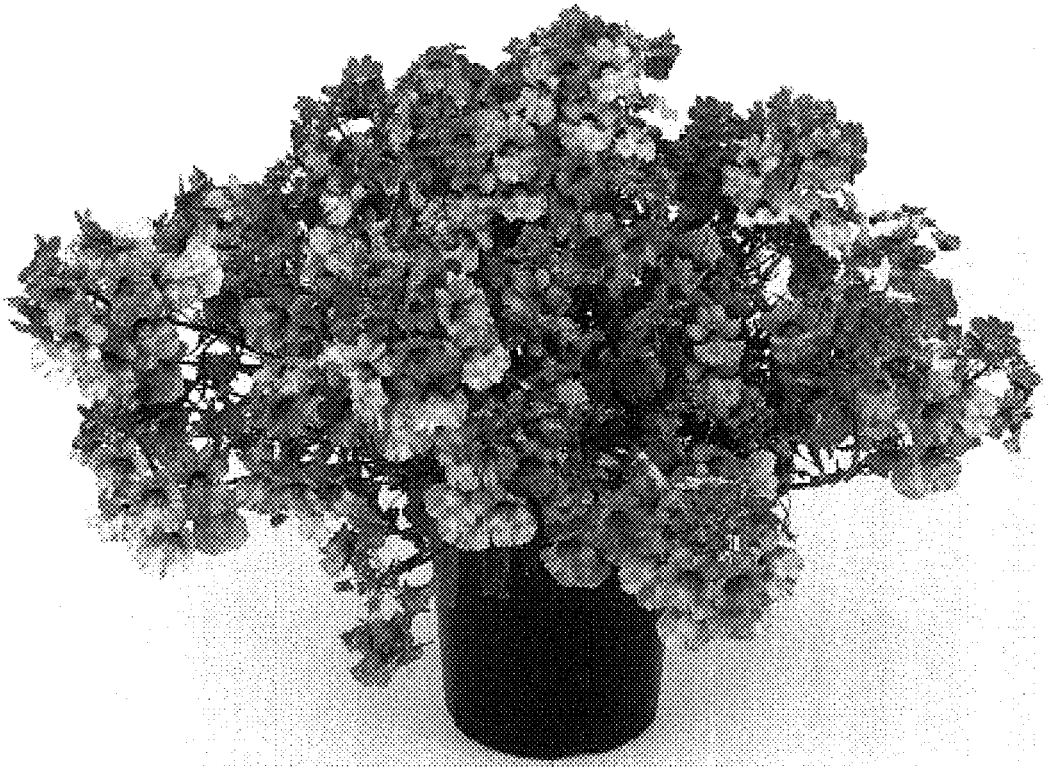

* * * * *